US007816316B2

(12) United States Patent
Hahn et al.

(10) Patent No.: US 7,816,316 B2
(45) Date of Patent: Oct. 19, 2010

(54) SUSTAINED RELEASE DRUG CARRIER

(75) Inventors: Sei Kwang Hahn, Gotenba (JP); Teruo Nakamura, Gotenba (JP); Tsuyoshi Shimoboji, Gotenba (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 628 days.

(21) Appl. No.: 10/536,031

(22) PCT Filed: Nov. 21, 2003

(86) PCT No.: PCT/JP03/14906

§ 371 (c)(1), (2), (4) Date: May 23, 2005

(87) PCT Pub. No.: WO2004/046200

PCT Pub. Date: Jun. 3, 2004

(65) Prior Publication Data

US 2006/0110458 A1    May 25, 2006

(30) Foreign Application Priority Data

Nov. 21, 2002   (JP)   .............................. 2002-338167

(51) Int. Cl.
A61K 38/02 (2006.01)
A61K 31/728 (2006.01)

(52) U.S. Cl. .......................................... 514/2; 514/23
(58) Field of Classification Search ..................... 514/2, 514/23

See application file for complete search history.

(56) References Cited

U.S. PATENT DOCUMENTS

| 4,582,865 | A | 4/1986 | Balazs et al. | |
|---|---|---|---|---|
| 5,827,937 | A | 10/1998 | Ågerup | |
| 5,874,417 | A | 2/1999 | Prestwich | |
| 2003/0012818 | A1* | 1/2003 | Schense et al. | 424/486 |
| 2005/0176620 | A1* | 8/2005 | Prestwich et al. | 514/2 |
| 2007/0031503 | A1* | 2/2007 | Hirakura et al. | 424/490 |

FOREIGN PATENT DOCUMENTS

| EP | 0 216 453 A2 | 4/1987 |
|---|---|---|
| EP | 0 265 116 A2 | 4/1988 |
| EP | 0 341 745 A1 | 11/1989 |
| JP | 01-156912 A | 6/1989 |
| JP | 05-140201 A | 6/1993 |
| JP | 08-301903 A | 11/1996 |
| JP | 09-59303 A | 3/1997 |
| JP | 10-67687 A | 3/1998 |
| WO | WO 94/02517 A1 | 2/1994 |
| WO | WO 95/15168 A1 | 6/1995 |
| WO | WO 95/25751 A1 | 9/1995 |
| WO | WO 98/08876 A1 | 3/1998 |
| WO | WO 98/45335 A1 | 10/1998 |
| WO | WO 00/44808 A1 | 8/2000 |
| WO | WO 00/46253 A1 | 8/2000 |
| WO | 02/068383 A2 | 9/2002 |

OTHER PUBLICATIONS

Shu, et. al., Disulfide Cross-Linked Hyaluronan Hydrogels, Biomacromolecules 2002, 3, 1304-1311.*
Carrasquillo, Karen, et al, "On the structural preservation of recombinant human growth hormone in a dried film of a synthetic biodegradable polymer", Journal of Pharmaceutical Sciences. (Feb. 1999). 88(2):166-173.
Crotts, G., and Tae Gwan Park, "Protein delivery from poly(lactic-co-glycolic acid) biodegradable microspheres: release kinetics and stability", Microencapsulation. (1998). 15(6):699-713.
Kato, Motohiro, et al, "The disposition of recombinant human erythroprotein (EPOCH) after subcutaneous administration (1): Pharmacokinetics of non-labeled EPOCH in rats an dogs", Xenobio. Metabol. and Disposition. (1993). 8:471-479.
Shu, Xiao Zheng, et al , "Disulfide cross-linked hyaluronan hydrogels", Biomacromolecules. (2003). 3:1304-1311.
Smeds, Kimberly, and Mark Grinstaff, "Photocrosslinkable polysaccharides for in situ hydrogel formation", Journal of Biomedical Materials Research. (2001). 54:115-121.
Supplementary European Search Report issued Feb. 12, 2010 in EP Appln No. 03774146.9.

* cited by examiner

Primary Examiner—Shaojia Anna Jiang
Assistant Examiner—Jonathan S Lau
(74) Attorney, Agent, or Firm—Browdy and Neimark, PLLC

(57) ABSTRACT

The present invention aims to provide completely biodegradable and biocompatible sustained-release carriers for proteins or peptides, which allow encapsulation of the proteins or peptides at high encapsulation rates without inhibiting their biological activity. The present invention provides a method for preparing a sustained-release carrier, wherein in a solution in the presence of a protein or a peptide, a hyaluronic acid derivative having an unsaturated bond(s) or a mercapto group(s) introduced into hyaluronic acid is chemically crosslinked with a mercapto group-containing compound or an unsaturated bond-containing compound, respectively, to give a hydrogel. The method of the present invention enables efficient encapsulation of proteins or peptides while retaining their biological activity.

6 Claims, 2 Drawing Sheets

SUSTAINED RELEASE DRUG CARRIER

TECHNICAL FIELD

The present invention relates to sustained-release drug carriers based on a hyaluronic acid hydrogel, which allow sustained release of proteins or peptides.

BACKGROUND ART

In recent years, an increasing number of formulations of pharmacologically active proteins or peptides have been developed for commercial use. However, such drugs usually have a short half-life in the blood and most of them are injections that must be administered repeatedly at frequent intervals, thus imposing excessive burdens on patients during drug administration. Hence, there is a demand for practical sustained-release formulations of protein or peptide drugs, which exert their efficacy in as small amounts as possible and which permit reduced frequency of administration.

Sustained-release formulations of pharmacologically active proteins or peptides will cause denaturation or aggregation of the proteins or peptides during formulation preparation or sustained release, which results in a reduced recovery rate and constitutes a major obstacle to their development for commercial use. It has been attempted to prepare sustained-release formulations based on a biodegradable polymer matrix such as polylactic acid-polyglycolic acid copolymer (PLGA), but such formulations have been reported to cause protein denaturation and/or aggregation due to the hydrophobicity of the matrix, a drying step and/or a decrease in pH (see J. Pharm. Sci. vol. 88, pp. 166-173, 1999 and J. Microencapsulation vol. 15, pp. 699-713, 1998). On the other hand, there are also reports of sustained-release formulations based on a hydrophilic hydrogel matrix with reduced risks of these problems, but such formulations are not ready for commercial use. In terms of safety, a material used as a sustained-release matrix should combine non-antigenicity, non-mutagenicity, non-toxicity and biodegradability. Thus, no sustained-release formulation is now ready for commercial use in all aspects, i.e., encapsulation rate and recovery rate of proteins or peptides, as well as safety.

Hyaluronic acid (HA), a biomaterial (polysaccharide) isolated from the vitreous body of bovine eyes in 1934 by K. Meyer, has been known as a major component of extracellular matrix for a long time. HA is a kind of glycosaminoglycan composed of disaccharide units in which D-glucuronic acid and N-acetylglucosamine are linked to one another via $\beta(1\rightarrow 3)$glycosidic linkages (Formula (VI)).

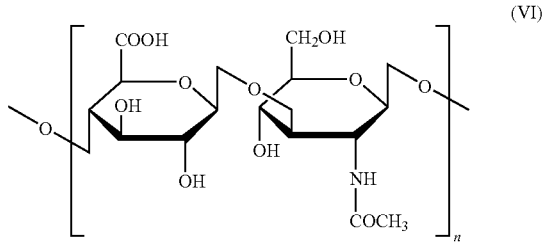

(VI)

There is no species difference in the chemical and physical structure of HA and humans also have a metabolic system for HA; HA is therefore the safest medical biomaterial in terms of immunogenicity and toxicity. Recently, microbial mass production of high-molecular-weight HA became possible allowing commercial use of HA in the fields of therapeutic agents for degenerated cartilage, cosmetics, etc.

There are also many reports on crosslinking techniques using hyaluronic acid as a matrix and sustained release of protein or peptide drugs from hyaluronic acid gels. Techniques known for gelling HA via chemical crosslinking include the carbodiimide method (see International Publication No. WO94/02517), the divinylsulfone method (see JP 61-138601 A), and the glycidyl ether method (see JP 05-140201 A). In general, when a protein or peptide is introduced into a crosslinked gel for encapsulation purposes, it results in a low introduction rate because of problems arising from compatibility and electrostatic repulsion between a hyaluronic acid derivative and the protein or peptide. In contrast, when in situ crosslinking is performed in the presence of a protein or peptide, it is advantageous in that the protein or peptide can be held in a gel at a high encapsulation rate. There are some reports showing that such in situ crosslinking is adapted for encapsulation of proteins or peptides into hyaluronic acid derivative gels to give sustained-release formulations (see, e.g., U.S. Pat. No. 5,827,937). However, there arises a problem of recovery rate when such an approach is used for in situ crosslinking of hyaluronic acid in the presence of proteins or peptides. As an example, a method is reported in which a hyaluronic acid derivative (HA-HZ) modified to have a hydrazide group (HZ) is crosslinked with a crosslinking agent comprising N-hydroxysuccinimide (NHS) (see International Publication No. WO95/15168). This method is intended for in situ crosslinking under physiological conditions and limits crosslinkage formation at pH 7.4 to pH 8.5. However, the inventors' investigations have shown that this method results in low recovery rates of proteins or peptides from the thus obtained hyaluronic acid derivative gel. This is because the proteins or peptides are partially reacted (mainly at their amino groups) with the crosslinking agent during crosslinking reaction resulting in crosslinked proteins. This method also suffers from a problem in that denatured proteins or peptides remaining in the gel have reduced biological activity and, if anything, are responsible for the development of antigenicity. It is an essential requirement for pharmaceutical preparations that the encapsulated drug is released at a high recovery rate, and no method is known for chemically crosslinking and gelling hyaluronic acid without causing proteins or peptides to react. Also, another method has been reported to encapsulate proteins or peptides at high recovery rates, in which polyethylene glycol (PEG) is used as a matrix and crosslinked through nucleophilic addition reaction of unsaturated functional groups (see International Publication No. WO00/44808), but this method suffers from a problem in that fragments of non-biodegradable polyethylene glycol remain in the resulting material.

DISCLOSURE OF THE INVENTION

As stated above, no method is known for preparing a biodegradable gel which allows in situ chemical crosslinking in the presence of proteins or peptides while retaining their biological activity and which satisfies a high encapsulation rate, a high recovery rate and safety by encapsulating the proteins or peptides into the hydrogel. Moreover, no example is known for sustained-release protein or peptide formulations prepared using such a gel.

As a result of extensive and intensive efforts made to overcome the problems stated above, the inventors of the present invention have found that when in a solution in the presence of a protein or a peptide, a hyaluronic acid derivative having an unsaturated bond-containing group(s) or a mercapto group(s) introduced into hyaluronic acid is chemically crosslinked with a mercapto group-containing compound or an unsaturated bond-containing compound, respectively, to give a hydrogel, such treatment enables efficient encapsulation of proteins or peptides while retaining their biological activity and enables the provision of biodegradable and safe sustained-release carriers for proteins or peptides. This finding led to the completion of the present invention.

Namely, in one aspect, the present invention provides a sustained-release drug carrier comprising a hydrogel of a hyaluronic acid derivative chemically crosslinked in a solution in the presence of a protein or a peptide, wherein the hyaluronic acid derivative has an unsaturated bond(s) introduced into hyaluronic acid and is chemically crosslinked with a mercapto group-containing compound or, alternatively, wherein the hyaluronic acid derivative has a mercapto group(s) introduced into hyaluronic acid and is chemically crosslinked with an unsaturated bond-containing compound.

In one aspect, the present invention provides a method for preparing such a hyaluronic acid derivative having a mercapto group(s) as mentioned above, which comprises the following steps:

(a) introducing a hydrazyl group(s) or an amino group(s) by converting at least one or more carboxyl groups of hyaluronic acid into N-substituted amide or ester group(s) having a substituent containing a hydrazyl or amino group; and (b) introducing a mercapto group(s) into the resulting hyaluronic acid derivative having a hydrazyl or amino group(s).

In this method, the hyaluronic acid derivative formed in step (a) is preferably a hyaluronic acid derivative whose molecule contains at least one or more repeated structures represented by Formula (I):

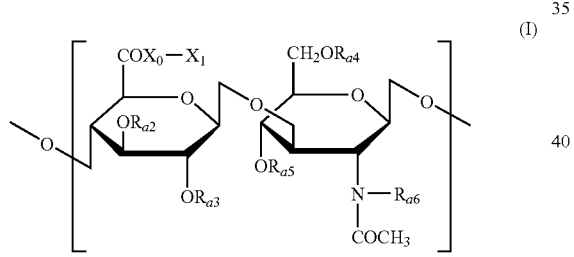

(I)

(wherein $X_0$ represents —O— or —N(—$R_1$)—, $R_1$ represents a hydrogen atom, a linear or branched $C_{1-10}$ alkyl group, a linear or branched $C_{1-10}$ hydroxyalkyl group, a polyalkylene oxide group, a polypeptide group, or a polyester group, $R_{a2}$, $R_{a3}$, $R_{a4}$, $R_{a5}$ and $R_{a6}$ each independently represent a hydrogen atom, a linear or branched $C_{1-6}$ alkyl group, a linear or branched $C_{1-6}$ alkenyl group, a linear or branched $C_{1-6}$ alkynyl group, a linear or branched $C_{1-6}$ alkylcarbonyl group, a linear or branched $C_{1-6}$ alkenylcarbonyl group, a linear or branched $C_{1-6}$ alkynylcarbonyl group, or —$SO_2OH$, $X_1$ represents —$Y_1$-$Q_1$-$Y_2$—NH—$R_2$ or —NH—$R_2$, $Y_1$ represents a single bond, —N(—$R_3$)CO—, —N(—$R_3$)—, —CO—, or —$CH_2$CO—, $Y_2$ represents a single bond, —CON(—$R_4$)—, or —N(—$R_4$)—, $Q_1$ represents a linear or branched $C_{1-10}$ alkylene group, a linear or branched $C_{1-10}$ hydroxyalkylene group, a polyalkylene oxide group, a polypeptide group, or a polyester group, and $R_2$, $R_3$ and $R_4$ each independently represent a hydrogen atom, a linear or branched $C_{1-10}$ alkyl group, a linear or branched $C_{1-10}$ hydroxyalkyl group, a polyalkylene oxide group, a polypeptide group, or a polyester group).

As used in Formula (I), the term "polyalkylene oxide group" refers to a group represented by —(CH(—R)$CH_2$O)$_n$—OH (wherein R represents a hydrogen atom or a $C_{1-5}$ alkyl group) and preferably represents a polyethylene oxide group or a polypropylene oxide group. Likewise, n is preferably an integer of 1 to 20. Although the polypeptide group is not limited in any way, it is preferably composed of 1 to 20 amino acids. Likewise, although the polyester group is not limited in any way, it is preferably a polyglycolic acid group or a polylactic acid group.

In Formula (I), $X_0$ preferably represents —N(—$R_1$)—. In Formula (I), $R_1$ preferably represents a hydrogen atom. In Formula (I), $X_1$ preferably represents —$Y_1$-$Q_1$-$Y_2$—NH—$R_2$. In Formula (I), $Y_1$ preferably represents a single bond or —N(—$R_3$)—. In Formula (I), $Y_2$ preferably represents a single bond. In Formula (I), $Q_1$ preferably represents a linear or branched $C_{1-4}$ alkylene group. In Formula (I), $R_2$ and $R_3$ each preferably represent a hydrogen atom.

In this method, the hyaluronic acid derivative formed in step (b) is preferably a hyaluronic acid derivative whose molecule contains at least one or more repeated structures represented by Formula (II):

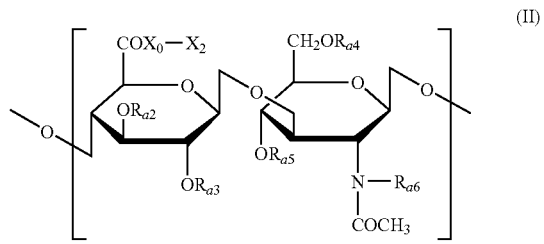

(II)

(wherein $X_2$ represents —$Y_1$-$Q_1$-$Y_2$—N(—$R_2$)—$Y_3$-$Q_2$-SH or —N(—$R_2$)—$Y_3$-$Q_2$-SH, $X_0$, $R_1$, $R_{a2}$, $R_{a3}$, $R_{a4}$, $R_{a5}$, $R_{a6}$, $Y_1$, $Y_2$, $Q_1$, $R_2$, $R_3$ and $R_4$ are as defined above for Formula (I), $Y_3$ represents a single bond, —CO—, —$C_6H_4$—, —$CO_2$—, —$SO_2$—, —$CH_2$—CH(OH)—, —C(=NH)—, —PO(OH)—O—, —CSNH—, or —CONH—, and $Q_2$ represents a linear or branched $C_{1-10}$ alkylene group, a linear or branched $C_{1-10}$ hydroxyalkylene group, a polyalkylene oxide group, a polypeptide group, or a polyester group).

In Formula (II), $X_0$ preferably represents —N(—$R_1$)—. In Formula (II), $R_1$ preferably represents a hydrogen atom. In Formula (II), $X_2$ preferably represents —$Y_1$-$Q_1$-$Y_2$—N(—$R_2$)—$Y_3$-$Q_2$-SH. In Formula (II), $Y_1$ preferably represents a single bond or —N(—$R_3$)—. In Formula (II), $Y_2$ preferably represents a single bond. In Formula (II), $Q_1$ preferably represents a linear or branched $C_{1-4}$ alkylene group. In Formula (II), $R_2$ and $R_3$ each preferably represent a hydrogen atom. In Formula (II), $Y_3$ preferably represents —CO—. In Formula (II), $Q_2$ preferably represents a linear or branched $C_{1-4}$ alkylene group.

In another aspect, the present invention provides a method for preparing such a hyaluronic acid derivative having a mercapto group(s) as mentioned above, which comprises the step of converting, in an organic solvent, at least one or more carboxyl groups of hyaluronic acid into N-substituted amide group(s) having a substituent containing a mercapto group.

In this method, the resulting hyaluronic acid derivative having a mercapto group(s) is preferably a hyaluronic acid derivative whose molecule contains at least one or more repeated structures represented by Formula (IIa):

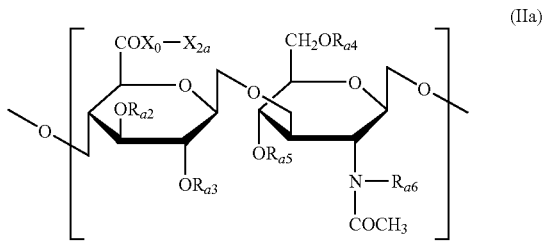

(wherein
$X_0$ represents —O— or —N(—$R_1$)—, $R_1$ represents a hydrogen atom, a linear or branched $C_{1-10}$ alkyl group, a linear or branched $C_{1-10}$ hydroxyalkyl group, a polyalkylene oxide group, a polypeptide group, or a polyester group, $R_{a2}$, $R_{a3}$, $R_{a4}$, $R_{a5}$ and $R_{a6}$ each independently represent a hydrogen atom, a linear or branched $C_{1-6}$ alkyl group, a linear or branched $C_{1-6}$ alkenyl group, a linear or branched $C_{1-6}$ alkynyl group, a linear or branched $C_{1-6}$ alkylcarbonyl group, a linear or branched $C_{1-6}$ alkenylcarbonyl group, a linear or branched $C_{1-6}$ alkynylcarbonyl group, or —$SO_2OH$, $X_{2a}$ represents —$Y_1$-$Q_1$-$Y_2$-$Q_3$-$Y_3$-$Q_2$-SH or —N(—$R_2$)—$Y_3$-$Q_2$-SH, $Y_1$ represents a single bond, —N(—$R_3$)CO—, —N(—$R_3$)—, —CO—, or —$CH_2$CO—, $Y_2$ and $Y_3$ each independently represent a single bond, —O—, —S—, —SO—, —$SO_2$—, —N(—$R_4$)—, —COO—, —OCO—, —CON(—$R_4$)—, —N(—$R_4$)CO—, or —N(—$R_4$)CON(—$R_5$)—, $Q_1$, $Q_2$ and $Q_3$ each independently represent a linear or branched $C_{1-10}$ alkylene group, a linear or branched $C_{1-10}$ hydroxyalkylene group, a polyalkylene oxide group, a polypeptide group, or a polyester group, and $R_2$, $R_3$, $R_4$ and $R_5$ each independently represent a hydrogen atom, a linear or branched $C_{1-10}$ alkyl group, a linear or branched $C_{1-10}$ hydroxyalkyl group, a polyalkylene oxide group, a polypeptide group, or a polyester group).

As used in Formula (IIa), the term "polyalkylene oxide group" refers to a group represented by —(CH(—R)$CH_2O)_n$—OH (wherein R represents a hydrogen atom or a $C_{1-5}$ alkyl group) and preferably represents a polyethylene oxide group or a polypropylene oxide group. Likewise, n is preferably an integer of 1 to 20. Although the polypeptide group is not limited in any way, it is preferably composed of 1 to 20 amino acids. Likewise, although the polyester group is not limited in any way, it is preferably a polyglycolic acid group or a polylactic acid group.

In Formula (IIa), $X_0$ preferably represents —N(—$R_1$)—. In Formula (IIa), $R_1$ preferably represents a hydrogen atom. In Formula (IIa), $X_{2a}$ preferably represents —$Y_1$-$Q_1$-$Y_2$-$Q_3$-$Y_3$-$Q_2$-SH. In Formula (IIa), $Y_1$ preferably represents a single bond or —N(—$R_3$)—. In Formula (IIa), $Y_2$ preferably represents a single bond. In Formula (IIa), $Y_3$ preferably represents a single bond. In Formula (IIa), $Q_1$, $Q_2$ and $Q_3$ each preferably represent a linear or branched $C_{1-4}$ alkylene group. In Formula (IIa), $R_2$ and $R_3$ each preferably represent a hydrogen atom. In Formula (IIa), $Y_3$ preferably represents —CO—.

In another aspect, the present invention provides a hyaluronic acid derivative having a mercapto group(s) prepared by the above method.

Moreover, the hyaluronic acid derivative having a mercapto group(s) preferably contains the repeated structure A represented by Formula (III):

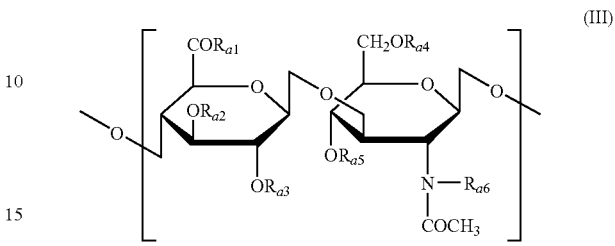

(wherein
$R_{a1}$ represents a hydroxyl group, an amino group which may be mono- or di-substituted with a linear or branched $C_{1-6}$ alkyl group, or a linear or branched $C_{1-6}$ alkoxy group, or $R_{a1}$ may form a carboxylate salt with a cation selected from the group consisting of sodium ion, potassium ion, calcium ion, magnesium ion, lithium ion and an optionally substituted ammonium ion, and $R_{a2}$, $R_{a3}$, $R_{a4}$, $R_{a5}$ and $R_{a6}$ each independently represent a hydrogen atom, a linear or branched $C_{1-6}$ alkyl group, a linear or branched $C_{1-6}$ alkenyl group, a linear or branched $C_{1-6}$ alkynyl group, a linear or branched $C_{1-6}$ alkylcarbonyl group, a linear or branched $C_{1-6}$ alkenylcarbonyl group, a linear or branched $C_{1-6}$ alkynylcarbonyl group, or —$SO_2OH$) and the repeated structure B represented by the above Formula (II) or (IIa), wherein the abundance ratio between these repeated structures A and B is preferably 95:5 to 10:90, more preferably 90:10 to 10:90, and even more preferably 80:20 to 20:80.

In yet another aspect, the present invention provides a method for preparing such a hyaluronic acid derivative having an unsaturated bond-containing group(s) as mentioned above, which comprises the following steps:

(a) introducing a hydrazyl group(s) or an amino group(s) by converting at least one or more carboxyl groups of hyaluronic acid into N-substituted amide group(s) having a substituent containing a hydrazyl or amino group; and (b) introducing an unsaturated bond-containing group(s) into the resulting hyaluronic acid derivative having a hydrazyl or amino group(s).

In this method, the hyaluronic acid derivative formed in step (a) is preferably a hyaluronic acid derivative whose molecule contains at least one or more repeated structures represented by the above Formula (I).

In this method, the hyaluronic acid derivative formed in step (b) is preferably a hyaluronic acid derivative whose molecule contains at least one or more repeated structures represented by Formula (IV):

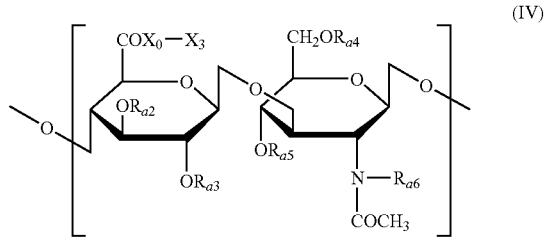

(wherein
$X_0$ represents —O— or —N(—$R_1$)—,
$X_3$ represents —$Y_1$-$Q_1$-$Y_2$—N(—$R_2$)—$Y_3$-$Q_4$ or —N(—$R_2$)—$Y_3$-$Q_4$,
$R_1$ represents a hydrogen atom, a linear or branched $C_{1-10}$ alkyl group, a linear or branched $C_{1-10}$ hydroxyalkyl group, a polyalkylene oxide group, a polypeptide group, or a polyester group,
$R_{a2}$, $R_{a3}$, $R_{a4}$, $R_{a5}$ and $R_{a6}$ each independently represent a hydrogen atom, a linear or branched $C_{1-6}$ alkyl group, a linear or branched $C_{1-6}$ alkenyl group, a linear or branched $C_{1-6}$ alkynyl group, a linear or branched $C_{1-6}$ alkylcarbonyl group, a linear or branched $C_{1-6}$ alkenylcarbonyl group, a linear or branched $C_{1-6}$ alkynylcarbonyl group, or —$SO_2OH$, $Y_1$ represents a single bond, —N(—$R_3$)CO—, —N(—$R_3$)—, —CO—, or —$CH_2CO$—,
$Y_2$ represents a single bond, —CON(—$R_4$)—, or —N(—$R_4$)—,
$Y_3$ represents a single bond, —CO—, —N(—$R_5$)CO—, —N(—$R_5$)—, or —$CH_2CO$—,
$Q_1$ represents a linear or branched $C_{1-10}$ alkylene group, a linear or branched $C_{1-10}$ hydroxyalkylene group, a polyalkylene oxide group, a polypeptide group, or a polyester group,
$R_2$, $R_3$, $R_4$ and $R_5$ each independently represent a hydrogen atom, a linear or branched $C_{1-10}$ alkyl group, a linear or branched $C_{1-10}$ hydroxyalkyl group, a polyalkylene oxide group, a polypeptide group, or a polyester group, and
$Q_4$ represents a linear or branched $C_{2-10}$ alkenyl group, or a linear or branched $C_{2-10}$ alkynyl group).

As used in Formula (IV), the term "polyalkylene oxide group" refers to a group represented by —(CH(—R)CH$_2$O)$_n$—OH (wherein R represents a hydrogen atom or a $C_{1-5}$ alkyl group) and preferably represents a polyethylene oxide group or a polypropylene oxide group. Likewise, n is preferably an integer of 1 to 20. Although the polypeptide group is not limited in any way, it is preferably composed of 1 to 20 amino acids. Likewise, although the polyester group is not limited in any way, it is preferably a polyglycolic acid group or a polylactic acid group.

In Formula (IV), $X_0$ preferably represents —N(—$R_1$)—. In Formula (IV), $R_1$ preferably represents a hydrogen atom. In Formula (IV), $X_3$ preferably represents —$Y_1$-$Q_1$-$Y_2$—N(—$R_2$)—$Y_3$-$Q_4$. In Formula (IV), $Y_1$ preferably represents a single bond, —N(—$R_3$)CO—, or —N(—$R_3$)—, and more preferably —N(—$R_3$)CO—. In Formula (IV), $Y_2$ preferably represents a single bond or —CON(—$R_3$)—, and more preferably —CON(—$R_3$)—. In Formula (IV), $Y_3$ preferably represents a single bond, —CO—, or —N(—$R_3$)—, and more preferably —CO—. In Formula (IV), $Q_1$ preferably represents a linear or branched $C_{1-4}$ alkylene group. In Formula (IV), $R_2$ and $R_3$ each preferably represent a hydrogen atom. In Formula (IV), $Q_4$ preferably represents a linear or branched $C_{2-10}$ alkenyl group.

In yet another aspect, the present invention provides a hyaluronic acid derivative having an unsaturated bond-containing group(s) prepared by the above method.

Moreover, the hyaluronic acid derivative having an unsaturated bond-containing group(s) preferably contains the repeated structure A represented by the above Formula (III) and the repeated structure C represented by the above Formula (IV), wherein the abundance ratio between these repeated structures A and C is 95:5 to 10:90, preferably 90:10 to 10:90, and more preferably 80:20 to 20:80.

In yet another aspect, the present invention provides a chemically crosslinked hyaluronic acid derivative formed by chemically crosslinking the above hyaluronic acid derivative having an unsaturated bond-containing group(s) with an unsaturated bond-containing compound, as well as a chemically crosslinked hyaluronic acid derivative formed by chemically crosslinking the above hyaluronic acid derivative having a mercapto group(s) with an unsaturated bond-containing compound.

The chemically crosslinked hyaluronic acid derivative is preferably a chemically crosslinked hyaluronic acid derivative whose molecule contains at least one or more repeated structures represented by Formula (V):

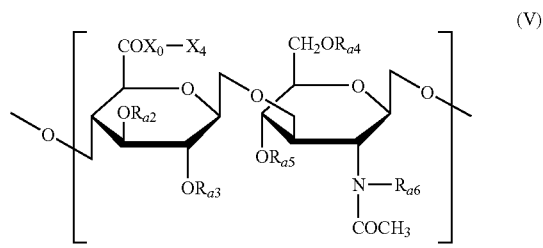

(wherein
$X_0$ represents —O— or —N(—$R_1$)—,
$R_1$ represents a hydrogen atom, a linear or branched $C_{1-6}$ alkyl group, a linear or branched $C_{1-10}$ hydroxyalkyl group, a polyalkylene oxide group, a polypeptide group, or a polyester group,
$R_{a2}$, $R_{a3}$, $R_{a4}$, $R_{a5}$ and $R_{a6}$ each independently represent a hydrogen atom, a linear or branched $C_{1-6}$ alkyl group, a linear or branched $C_{1-6}$ alkenyl group, a linear or branched $C_{1-6}$ alkynyl group, a linear or branched $C_{1-6}$ alkylcarbonyl group, a linear or branched $C_{1-6}$ alkenylcarbonyl group, a linear or branched $C_{1-6}$ alkynylcarbonyl group, or —$SO_2OH$,
$X_4$ represents —$Y_1$-$Q_1$-$Y_2$—$X_5$—$Y_3$-$Q_2$-S-L or —N(—$R_2$)—$Y_3$-$Q_2$-S-L,
$X_5$ represents -$Q_3$- or —N(—$R_2$)—,
$Y_1$ represents a single bond, —N(—$R_3$)CO—, —N(—$R_3$)—, —CO—, or —$CH_2CO$—,
$Y_2$ represents a single bond, —O—, —S—, —SO—, —$SO_2$—, —N(—$R_4$)—, —COO—, —OCO—, —CON(—$R_4$)—, —N(—$R_4$)CO—, or —N(—$R_4$)CON(—$R_5$)—,
$Y_3$ represents a single bond, —CO—, —$C_6H_4$—, —$CO_2$—, —$SO_2$—, —$CH_2$—CH(OH)—, —C(=NH)—, —PO(OH)—O—, —CSNH—, or —CONH—,
$Q_1$, $Q_2$ and $Q_3$ each independently represent a linear or branched $C_{1-10}$ alkylene group, a linear or branched $C_{1-10}$ hydroxyalkylene group, a polyalkylene oxide group, a polypeptide group, or a polyester group,
$R_2$ and $R_3$ each independently represent a hydrogen atom, a linear or branched $C_{1-10}$ alkyl group, a linear or branched $C_{1-10}$ hydroxyalkyl group, a polyalkylene oxide group, a polypeptide group, or a polyester group,
L represents a linear or branched $C_{1-10}$ alkylene group, a linear or branched $C_{1-10}$ alkenylene group, or a polyethylene oxide group, each of which forms an intramolecular or intermolecular crosslinkage together with L in another repeated structure and which may optionally contain $Z_1$, $Z_2$, $Z_3$, $Z_4$ and $Z_5$ at the end of or within its main chain,
$Z_1$, $Z_2$, $Z_3$, $Z_4$ and $Z_5$ each independently represent —O—, —S—, —SO—, —$SO_2$—, —N(—$R_4$)—, —CH(—$R_6$)—, —C(—$R_6$)(—$R_7$)—, —CO—, —COO—, —OCO—, —CON(—$R_4$)—, —N(—$R_4$)CO—, or —N(—$R_4$)CON(—$R_5$)—,
$R_4$ and $R_5$ each independently represent a hydrogen atom, a linear or branched $C_{1-10}$ alkyl group, a linear or branched $C_{1-10}$ hydroxyalkylene group, a polyalkylene oxide group, a polypeptide group, or a polyester group, and $R_6$ and $R_7$ each independently represent a hydroxyl group, a linear or branched $C_{1-4}$ alkoxy group, a halogen atom, a carboxyl group, an amide group, or an ester group).

As used in Formula (V), the term "polyalkylene oxide group" refers to a group represented by —(CH(—R)CH$_2$O)$_n$—OH (wherein R represents a hydrogen atom or a $C_{1-5}$ alkyl group) and preferably represents a polyethylene oxide group or a polypropylene oxide group. Likewise, n is preferably an integer of 1 to 20. Although the polypeptide group is not limited in any way, it is preferably composed of 1 to 20 amino acids. Likewise, although the polyester group is not limited in any way, it is preferably a polyglycolic acid group or a polylactic acid group.

In Formula (V), $X_0$ preferably represents —N(—R$_1$)—. In Formula (V), $R_1$ preferably represents a hydrogen atom. In Formula (V), $X_4$ preferably represents —Y$_1$-Q$_1$-Y$_2$—X$_5$—Y$_3$-Q$_2$-S-L. In Formula (V), $X_5$ preferably represents —N(—R$_2$)—. In Formula (V), $Y_1$ preferably represents a single bond, —N(—R$_3$)CO—, or —N(—R$_3$)—, and more preferably —N(—R$_3$)CO—. In Formula (V), $Y_2$ preferably represents a single bond or —CON(—R$_3$)—, and more preferably —CON(—R$_3$)—. In Formula (V), $Y_3$ preferably represents a single bond, —CO—, or —N(—R$_3$)—, and more preferably —CO—. In Formula (V), $Q_1$ preferably represents a linear or branched $C_{1-4}$ alkylene group. In Formula (V), $R_2$ and $R_3$ each preferably represent a hydrogen atom. In Formula (V), $Q_2$ and $Q_3$ each preferably represent a linear or branched $C_{1-4}$ alkylene group. In Formula (V), L preferably represents a linear or branched $C_{1-4}$ alkylene group which may be substituted with one or more hydroxyl groups, carboxyl groups or linear or branched $C_{1-4}$ alkyl groups, and more preferably a linear or branched $C_{1-4}$ alkylene group.

The chemically crosslinked hyaluronic acid derivative preferably contains the repeated structure A represented by the above Formula (III) and the repeated structure D represented by the above Formula (V), wherein the abundance ratio between these repeated structures A and D is preferably 95:5 to 10:90, more preferably 90:10 to 10:90, and even more preferably 80:20 to 20:80.

PREFERRED MODE FOR CARRYING OUT THE INVENTION

Figure 1:
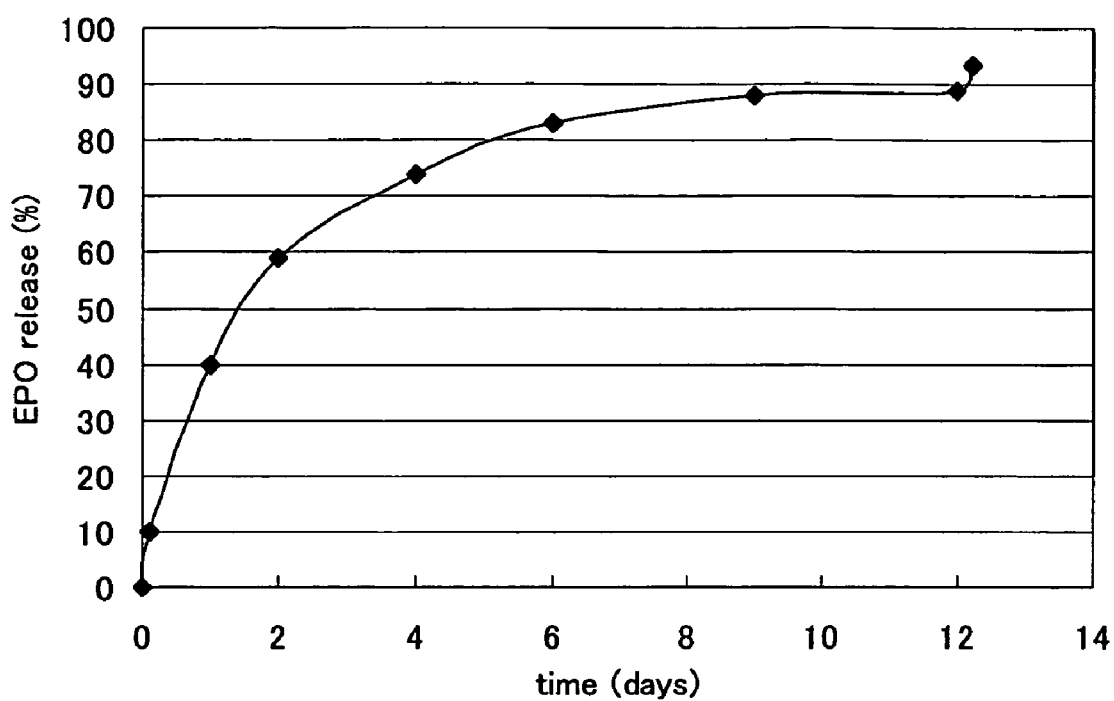
FIG. 1 shows an example of the results obtained for the determination of EPO release in buffer, as measured by RP-HPLC of 200 μL aliquots sampled over time from the gel of Example 2, which has been incubated in 2 mL PBS at 37° C.

The present invention will be further described in more detail below.

The sustained-release drug carrier of the present invention is characterized by comprising a hydrogel of a hyaluronic acid derivative chemically crosslinked in a solution in the presence of a protein or a peptide, wherein the hyaluronic acid derivative has an unsaturated bond(s) introduced into hyaluronic acid and is chemically crosslinked with a mercapto group-containing compound or, alternatively, wherein the hyaluronic acid derivative has a mercapto group(s) introduced into hyaluronic acid and is chemically crosslinked with an unsaturated bond-containing compound.

The sustained-release drug carrier of the present invention has excellent characteristics as shown below.

1. The carrier can offer complete biodegradability and in vivo safety.

2. By grafting with a functional group(s) crosslinkable to HA, the carrier can keep a very short distance between crosslinking points (about 3 nm when graft at 33 mol % based on glucuronic acid) and is advantageous in achieving long-term sustained release.

3. The carrier has a high crosslinking density.

4. The carrier can prevent protein denaturation.

The term "chemical(ly) crosslinking" or "chemically crosslinked" is intended to mean containing intermolecular or intramolecular crosslinkages via covalent bonds. It also means having both intermolecular and intramolecular crosslinkages.

The pH during crosslinking is not limited in any way, but it is preferably a pH at which the selective reaction between unsaturated bond and mercapto group preferentially occurs without causing protein or peptide denaturation preventing reactions with amino groups contained in proteins or peptides. Although such a pH can be selected as appropriate by those skilled in the art, it ranges from pH 3.0 to 9.0, preferably pH 6.0 to 8.5, by way of example.

An unsaturated bond to be introduced into hyaluronic acid or contained in a crosslinking agent may be a C—C double bond or a C—C triple bond, as well as a C=O bond or a —C=N— bond. Examples of an unsaturated bond-containing group include, without any limitation, a methacryloyl group, an acryloyl group, a maleimide group, a vinylsulfone group, and an acetylenecarbonyl group.

The crosslinking agent used for introduction of an unsaturated bond-containing group into hyaluronic acid may be a compound whose molecule contains two or more mercapto groups capable of reacting with an unsaturated bond via nucleophilic addition reaction. Examples include dithiothreitol (DTT), butanedithiol, polyethylene glycol dithiol, and a peptide having two or more cysteines.

The crosslinking agent used for introduction of a mercapto group into hyaluronic acid may be a compound whose molecule contains two or more unsaturated bond-containing groups capable of reacting with a mercapto group via nucleophilic addition reaction. Examples include ethylene glycol dimethacrylate, ethylenebisacrylamide, tris-2-maleimidoethylamine, 1,8-bismaleimidotriethylene glycol, and 1,4-bis-maleimidyl-2,3-dihydroxybutane.

Moreover, it is preferable to add a basic compound for the purpose of improving the stability of proteins or peptides during crosslinking reaction and improving the reaction velocity. Examples of a basic compound available for use include, without any limitation, carbonate salts (e.g., sodium carbonate, sodium bicarbonate), hydroxides (e.g., sodium hydroxide), and amines (e.g., aqueous ammonia, pyridine, triethylamine, ethylenediamine, ethanolamine, diethanolamine, triethanolamine). Among them, amines are preferred for use and triethanolamine is more preferred for use.

The preferred concentration for this purpose is 10 to 20 μL/mL.

If unreacted mercapto groups remain for a long time after completion of the crosslinking reaction, such groups facilitate protein denaturation. It is therefore preferable to remove unreacted mercapto groups, e.g., by washing off the unreacted mercapto groups immediately after gel preparation or by adding a compound (e.g., iodoacetic acid) capable of selectively reacting with a mercapto group. In addition, there is a possibility that only one end of a crosslinking agent is grafted onto a hyaluronic acid derivative to leave a residual reactive mercapto group(s), which in turn leads to protein denaturation. To remove such a free mercapto group, it is also preferable to add a compound capable of selectively reacting with a mercapto group.

There is no particular limitation on the method for preparing a hyaluronic acid derivative having an unsaturated bond-containing group(s), but it is difficult to achieve a high introduction rate, e.g., when glycidyl ether methacrylate or methacrylic anhydride is directly reacted with a hydroxyl group of HA (J. Biomed. Mat. Res. 54, 115-121, 2001). This is because hyaluronic acid will form a higher order structure in an aqueous solution by the action of hydrogen bonding or hydrophobic interaction to reduce the reactivity of its functional groups including hydroxyl and carboxylic acid groups. A higher crosslinking density is desired to achieve prolonged sustained release of proteins or peptides. To this end, it is desirable to introduce a substituent at the carboxyl group of the glucuronic acid moiety. For example, hyaluronic acid may be converted into a tertiary ammonium salt form, dissolved in a polar organic solvent such as dimethyl sulfoxide (DMSO), and then reacted with an unsaturated bond-containing amine or hydrazide in the presence of a coupling agent such as 1-ethyl-3-(3-dimethylaminopropyl)carbodiimide (EDC) to prepare the desired derivative.

Examples of such an unsaturated bond-containing amine include, without any limitation, allylamine, diallylamine, 4-amino-1-butene, acrylhydrazide, and methacrylhydrazide.

In light of achieving a high crosslinking density as stated above, it is preferable to introduce an amino group or a hydrazide group and then introduce an unsaturated bond-containing group into this amino or hydrazide group.

For example, carboxylic acid in hyaluronic acid may be condensed with adipic acid dihydrazide (ADH) or a divalent compound containing hydrazide or amino groups (e.g., ethylenediamine) in the presence of a condensing agent (e.g., EDC) to synthesize a hydrazide group-modified hyaluronic acid derivative (HA-HZ) or an amino group-modified hyaluronic acid derivative (HA-amino group), which may then be reacted with methacrylic anhydride.

Although there is no particular limitation on the method for preparing a hyaluronic acid derivative having a mercapto group(s), for example, hyaluronic acid may be converted into a tertiary ammonium salt form, dissolved in a polar organic solvent such as dimethyl sulfoxide (DMSO), and then reacted with a mercapto group-containing amine or hydrazide in the presence of a coupling agent such as 1-ethyl-3-(3-dimethylaminopropyl)carbodiimide (EDC) to prepare the desired derivative.

Examples of such a mercapto group-containing amine include, without any limitation, 2-aminoethane-1-thiol, 3-aminopropane-1-thiol, and thioglycolic acid hydrazide.

For the reason that a high crosslinking density can be achieved, it is preferable to introduce an amino group or a hydrazide group at first and then introduce a mercapto group into this amino or hydrazide group. For example, carboxylic acid in hyaluronic acid may be condensed with adipic acid dihydrazide (ADH) or a divalent compound containing hydrazide or amino groups (e.g., ethylenediamine) in the presence of a condensing agent such as 1-ethyl-3-(3-dimethylaminopropyl)carbodiimide (EDC) to synthesize a hydrazide group-modified hyaluronic acid derivative (HA-HZ) or an amino group-modified hyaluronic acid derivative (HA-amino group), which may then be reacted with, e.g., N-succinimidyl-3-[2-pyridyldithio]propionate (SPDP) and treated with a reducing agent (e.g., DTT) to form a mercapto group.

Although there is no particular limitation on the rate of hydrazide groups introduced into a hyaluronic acid derivative, usually in order to obtain a non-flowable gel, it is preferably 5 mol % or more, particularly preferably 10 mol % or more, based on glucuronic acid in the hyaluronic acid derivative.

In order to obtain a non-flowable gel, the rate of amino groups introduced into a hyaluronic acid derivative is 5 mol % or more, preferably 10 mol % or more, based on glucuronic acid in HA.

Although there is no particular limitation on the rate of unsaturated bond-containing groups introduced into a hyaluronic acid derivative, in order to obtain a non-flowable gel, it is preferably 5 mol % or more, particularly preferably 10 mol % or more, based on glucuronic acid in the hyaluronic acid derivative.

Although there is no particular limitation on the rate of mercapto groups introduced into a hyaluronic acid derivative, in order to obtain a non-flowable gel, it is 5 mol % or more, preferably 10 mol % or more, based on glucuronic acid in hyaluronic acid.

In a case where hyaluronic acid is crosslinked via mercapto groups after introduction of unsaturated bond-containing groups, the ratio of mercapto groups to unsaturated bond-containing groups is not limited in any way and can be selected as appropriate by those skilled in the art. However, the ratio of mercapto groups to unsaturated bonds is preferably 3:1 to 1:1, more preferably 2:1 to 1.5:1, in order to minimize reactions with proteins or peptides, to prevent unsaturated bond-containing groups from remaining in the gel and to ensure rapid reaction.

In a case where hyaluronic acid is crosslinked via unsaturated bond-containing groups after introduction of mercapto groups, the ratio of unsaturated bond-containing groups to mercapto groups is not limited in any way and can be selected as appropriate by those skilled in the art. However, the ratio of unsaturated bonds to mercapto groups is preferably 3:1 to 1:1, more preferably 2:1 to 1.5:1, in order to minimize reactions with proteins or peptides, to prevent unsaturated bond-containing groups from remaining in the gel and to ensure rapid reaction.

To prepare a hydrogel comprising a HA derivative and a pharmacologically active protein or peptide, for example, the HA derivative and the protein or peptide may be dissolved in phosphate-buffered physiological saline. A crosslinking agent may then be added to and dispersed uniformly in the resulting solution, followed by reaction at room temperature or 4° C. Because of its relatively low reaction velocity, this crosslinking method is advantageous in ensuring more uniform crosslinking of HA and preparing a uniform gel. This is effective for stabilization and prolongation of sustained release performance.

Hyaluronic acid used in the present invention may be of any origin, including those extracted from animal tissues, those obtained by fermentation techniques, and those chemically synthesized. Moreover, further treatment (e.g., hydrolysis) may be performed on hyaluronic acid.

Modified HA prepared in various manners and its salts with alkali metals (e.g., sodium, potassium, lithium) also fall within the scope of HA according to the present invention. Although HA is often modified at its carboxyl or hydroxyl group, the modified HA according to the present invention may be modified at any moiety. Such modified HA is not limited in any way and may receive any modification. Examples include sulfated HA (International Publication No.

WO95/25751), N-sulfated HA (International Publication No. WO98/45335), esterified HA (European Patent Publication No. 0216453, International Publication No. WO98/08876, European Patent Publication No. 0341745), periodate-oxidized HA, and amide-modified HA.

There is no particular limitation on the molecular weight of hyaluronic acid used in the present invention, and it is possible to use hyaluronic acid of any molecular weight. In general, hyaluronic acid of 5,000 to 3,500,000 daltons, preferably 10,000 to 2,000,000 daltons, can be used.

Examples of a pharmacologically active protein or peptide include, without any limitation, erythropoietin (EPO), granulocyte colony-stimulating factor (G-CSF), interferons-α, β and γ(INF-α, β, γ), thrombopoietin (TPO), ciliary neurotrophic factor (CNTF), tumor necrosis factor binding protein (TNFbp), interleukin-10 (IL-10), FMS-like tyrosine kinase (Flt-3), growth hormone (GH), insulin, insulin-like growth factor-1 (IGF-1), platelet-derived growth factor (PDFG), interleukin-1 receptor antagonist (IL-1ra), brain-derived neurotrophic factor (BDNF), keratinocyte growth factor (KGF), stem cell factor (SCF), megakaryocyte growth and defferenciation factor (MGDF), osteoprotegerin (OPG), leptin, parathyroid hormone (PTH), basic fibroblast growth factor (b-FGF), bone morphogenetic protein (BMP), glucagon-like peptide-1 (GLP-1), antibody, and diabody.

The hyaluronic acid derivative gel of the present invention is not limited in any way and may be a hydrosol or an organosol, preferably a hydrosol.

The sustained-release carrier of the present invention may be administered as a pharmaceutical composition in any dosage form suitable for the intended route of administration, in combination with one or more pharmaceutically acceptable diluents, wetting agents, emulsifiers, dispersants, auxiliaries, antiseptics, buffers, binders, stabilizers and the like. The route of administration may be either parenteral or oral.

To obtain injectable microparticles of the hyaluronic acid derivative, known techniques can be used, including those in which the gelled derivative is dried, frozen and then ground, those in which a gel in a microparticulate form is prepared using the emulsion method and then dried, those which are used for preparation of dry microparticles (e.g., the spray-drying method, the supercritical solution method), and those in which this composition is administered in a solution form before completion of the crosslinking reaction and then crosslinked in vivo.

EXAMPLES

Preparation of EPO-Encapsulating Hyaluronic Acid (HA) Derivative Hydrogels

The present invention will be further described in more detail in the following preferred examples, which are not intended to limit the scope of the invention.

NMR measurement was carried out using a nuclear magnetic resonance system JNM-ECA500 (JEOL. Ltd., Japan) and heavy water as a solvent. The introduction rate of each substituent was determined from the integral ratio between a peak unique to the introduced substituent and a peak derived from hyaluronic acid.

High performance liquid chromatography analysis on a reversed-phase column (RP-HPLC) was carried out using a Waters 600S controller, a 717 plus autosampler and a 486 ultraviolet photometric detector (Waters) under the following measurement conditions.

Column: C4 (particle diameter: 5 μm, size: 4.6×250 mm)

Mobile phases: A: water/acetonitrile/trifluoroacetic acid=400/100/1, B: water/acetonitrile/trifluoroacetic acid=100/400/1

Flow rate: 1 mL/minute, eluted with a gradient of the mobile phases A/B=65/35 to 0/100

Column temperature: around room temperature

Sample temperature: 4° C.

Detection wavelength: UV 280 nm

Analysis software: Millenium 32 ver. 3.21

Example 1

Example 1-1

Synthesis of Hydrazide (HZ) Group-Modified Hyaluronic Acid (HA-HZ)

Hyaluronic acid (HA) having a molecular weight of $1.9 \times 10^5$ daltons (200 mg, Denki Kagaku Kogyo Kabushiki Kaisha, Japan) was dissolved in distilled water at a concentration of 0.5% and adjusted with 5N hydrochloric acid to pH 4.7 to 4.8. 1-Ethyl-3-(3-dimethylaminopropyl)carbodiimide (EDC) and adipic acid dihydrazide (ADH) were added at a molar ratio of HA:EDC:ADH=1:0.3:40 (Batch 1-1), 1:1:40 (Batch 1-2) or 1:5:40 (Batch 1-3), and reacted while stirring at room temperature for 2 hours and adjusting the mixture with 5N hydrochloric acid to maintain a pH of 4.7 to 4.8. The reaction mixture was dialyzed against a 100 mM sodium chloride solution and a 25% ethanol solution (SpectraPor 7, molecular weight cutoff (MWCO): 12 k-14 k daltons) and lyophilized to give the titled HA-HZ.

The introduction rate of HZ in the resulting HA-HZ was determined for each batch by proton NMR, indicating that carboxylic acid in HA was modified with HZ at a content of 26% (Batch 1-1), 46% (Batch 1-2) or 69% (Batch 1-3) (calculated from comparison of N-acetyl groups in HA and HA-HZ, 2.1 ppm (3H) and methylene groups in the adipic acid-derived moiety of HA-HZ, 1.7 ppm, 2.4 ppm (2H each)).

Example 1-2

Synthesis of Methacryloyl (MA) Group-Modified Hyaluronic Acid (HA-MA)

HA-HZ obtained in Batches 1 to 3 of Example 1-1 (90 mg each) was dissolved in 0.45 mL of 100 mM phosphate buffer, pH 8 (HA-HZ 2% w/v), followed by addition of 0.54 mL methacrylic anhydride. The mixture was reacted while stirring at room temperature for 1 day and precipitated in ethanol, followed by washing with ethanol and drying. The introduction rate of MA in the resulting HA-MA was determined for each batch by proton NMR and the results obtained are shown in Table 1 (calculated from comparison of N-acetyl groups in HA and HA-MA, 2.1 ppm (3H) and vinyl protons of methacryloyl groups in HA-MA, 5.5-6.0 ppm (2H)).

TABLE 1

|  | Control | Batch 1 | Batch 2 | Batch 3 |
|---|---|---|---|---|
| HZ introduction | 0% | 26% | 46% | 69% |
| MA introduction | 4% | 12% | 17% | 29% |

Example 1-3

Preparation of EPO-Encapsulating HA Hydrogels

HA-MA (introduction rate of MA: 29%) obtained in Batch 3 of Example 1-2 (11 mg) and EPO (100 μg) were dissolved in 0.25 mL phosphate buffered saline (pH 7.4, PBS) (stirring at room temperature for 1 hour), followed by addition of 3.5 μL triethanolamine (TEA) and 10 μL dithiothreitol (DTT) solution (92.55 mg/mL in PBS). The mixture was reacted at room temperature for 3 hours to give a gel. The resulting gel was dialyzed against 400 mL PBS for 3 hours to wash off unreacted DTT.

Example 2

The same procedure as shown in Example 1-3 was repeated to prepare an EPO-encapsulating HA hydrogel, except that the gel prepared in Example 1-3 was supplemented with 10 μL iodoacetic acid solution (223.2 mg/mL in PBS, 2-fold molar excess over DTT) instead of being dialyzed.

Example 3

In Situ Crosslinked EPO-Encapsulating HA Hydrogels

Figure 2:
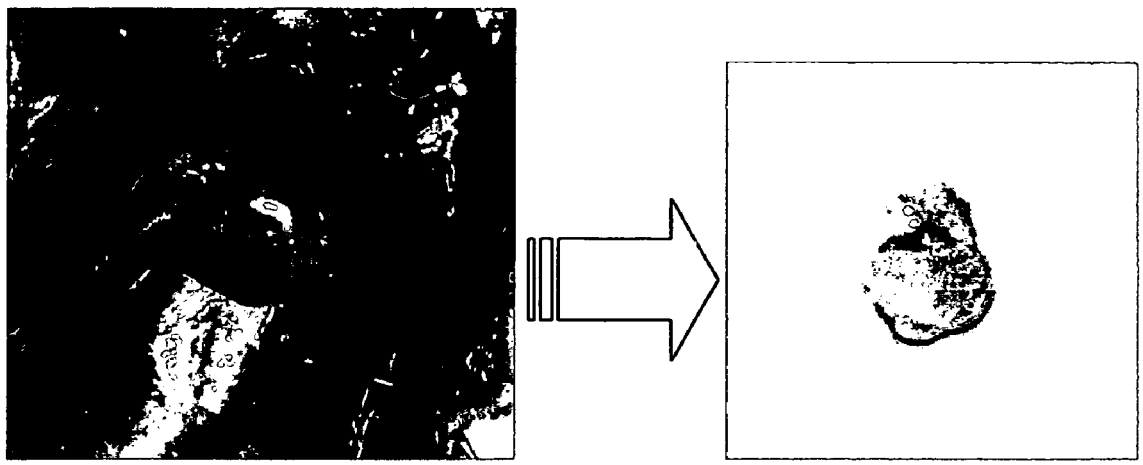
FIG. 2 presents a photograph showing a state when a rat is subcutaneously injected with a solution containing the hyaluronic acid derivative of the present invention, along with a photograph showing an example of the gel collected from the rat.

HA-MA (introduction rate of MA: 29%) obtained in Batch 2 of Example 1-2 (22 mg) and EPO (400 μg) were dissolved in 0.48 mL phosphate buffered saline (pH 7.4, PBS) (stirring at room temperature for 1 hour), followed by addition of 3.5 μL triethanolamine (TEA) and 20 μL dithiothreitol (DTT) (92.55 mg/mL). After stirring at room temperature for 10 minutes, the resulting solution was filled into a 1 mL syringe and then subcutaneously administered to rats in 100 μL volumes (using a 22-gauge needle) at 120 minutes after addition of DTT. After 4 hours, the gels were collected from the subcutaneous tissue of the rats. FIG. 2 presents photographs showing a state of the solution subcutaneously injected into the rats and the gel collected from the rats. This figure indicates that the solution with this composition is crosslinked and gelled in the subcutaneous tissue.

Comparative Example 1

The same procedure as shown in Example 1-3 was repeated to prepare an EPO-encapsulating HA hydrogel, except that 20 μL of dithiothreitol (DTT) (92.55 mg/mL) was added and reacted in PBS (pH 8.0), but TEA was not used in the preparation of EPO-encapsulating HA hydrogels according to Example 1.

Comparative Example 2

The same procedure as shown in Example 1 was repeated to prepare an EPO-encapsulating HA hydrogel, except that 5 μL of dithiothreitol (DTT) (92.55 mg/mL) was added and reacted in PBS (pH 8.0), but TEA was not used in the preparation of EPO-encapsulating HA hydrogels according to Example 1.

Comparative Example 3

The same procedure as shown in Example 1 was repeated to prepare an EPO-encapsulating HA hydrogel, except that 10 μL of dithiothreitol (DTT) (92.55 mg/mL) was added and reacted in PBS (pH 8.0), but TEA was not used in the preparation of EPO-encapsulating HA hydrogels according to Example 1.

Test Example 1

Measurement of EPO Recovery Rate in EPO-Encapsulating HA Hydrogels

The gels prepared in Examples 1 and 2 and Comparative Examples 1 to 3 (0.25 mL each, containing 100 μg/mL EPO) were each supplemented with 0.75 mL PBS (pH 7.4) containing 0.5 units of Hyaluronidase SD (Seikagaku Corporation, Japan) and enzymatically treated at 25° C. for 3 hours to completely digest the gels. The resulting solutions after enzymatic treatment (0.15 mL each) were used as sample solutions. These sample solutions were measured by reversed-phase high performance liquid chromatography (RP-HPLC) using a 0.1 mg/mL aqueous EPO solution as a standard solution to calculate the EPO concentration in each sample solution from the peak area ratio between standard solution and sample solution. The recovery rate was calculated as the amount of EPO determined by RP-HPLC relative to the amount of EPO added (0.1 mg/gel).

Table 2 shows the recovery rate of EPO collected from each gel relative to the initial amount of EPO, along with the time required for gelling.

TABLE 2

| Sample | Reaction time | EPO recovery rate |
|---|---|---|
| Example 1 | 3 hrs | 90% |
| Example 2 | 3 hrs | 92% |
| Comparative Example 1 | 5 hrs | 75% |
| Comparative Example 2 | 1 day | 71% |
| Comparative Example 3 | 6 to 7 hrs | 78% |

Test Example 2

Sustained Release of EPO from the Prepared EPO-Encapsulating HA Hydrogels

The gel prepared in Example 2 was incubated in 2 mL PBS at 37° C. and sampled over time in 200 μL aliquots. The amount of EPO released into the buffer was determined by RP-HPLC.

FIG. 1 shows the release profile of EPO from the gel, as determined by assuming that EPO collected from the gel after degradation with hyaluronidase immediately after preparation is set to 100%. After 12 days, hyaluronidase was added. The results indicate that EPO in the gel remains undenatured, 90% or more of which is sustained released.

By using the hyaluronic acid crosslinking method illustrated in the above Examples, proteins or peptides can be encapsulated in hydrogels during the in situ crosslinking reaction while retaining their biological activity to prepare sustained-release protein or peptide formulations.

Test Example 3

Sustained Release Performance of EPO from In Situ Crosslinked EPO-Encapsulating HA Hydrogels After addition of DTT, the prepared solution from Example 3 was allowed to stand at room temperature for 150 minutes and then subcutaneously administered to rats in 120 μL volumes. The serum EPO concentration was measured with an ELISA kit (Roche Diagnistics GmbH, Mannheim, Germany). Table 3 shows the mean residence time (MRT) analyzed by a non-compartment model using WinNonlin ver. 2.1 (Pharsight), along with MRT of controls, i.e., an EPO solution and an EPO+HA solution (molecular weight of HA: 2,000,000 daltons, 1% concentration). The analysis data of the EPO solution shown in Table 3 was calculated from dose-corrected simulation data of the reported value (Motohiro Kato, The disposition of recombinant human erythropoietin (EPOCH) after subcutaneous administration (1): Pharmacokinetics of non-labeled EPOCH in rats and dogs upon single administration; Xenobiotic Metabolism and Disposition, 8[4], 471-479, 1993). The tested crosslinked gel resulted in a prolonged period of EPO release.

TABLE 3

| | MRT (days) |
|---|---|
| EPO solution | 0.675 |
| EPO + HA solution | 0.924 |
| In situ crosslinked EPO-encapsulating HA hydrogel | 1.54 |

INDUSTRIAL APPLICABILITY

The sustained-release drug carrier of the present invention allows encapsulation of proteins or peptides into HA hydrogels during in situ chemical crosslinking of the HA derivative while retaining their biological activity, and enables sustained release of the proteins or peptides with high recovery rates.

The invention claimed is:
1. A sustained-release drug carrier, which comprises
a hydrogel of a hyaluronic acid derivative chemically crosslinked in a solution in the presence of a pharmacologically active protein or peptide dissolved in the solution,
wherein the hyaluronic acid derivative has an unsaturated C—C bond(s) introduced into hyaluronic acid and is chemically crosslinked by nucleophilic addition with a mercapto group-containing compound to form crosslinking between hyaluronic acid derivative molecules.
2. The sustained-release drug carrier of claim 1, wherein the unsaturated C—C bond(s) is selected from the group consisting of a methacryloyl group, an acryloyl group, a maleimide group, a vinylsulfonyl group, and a acetylenecarbonyl group.
3. The sustained-release drug carrier of claim 1, wherein said hyaluronic acid derivative is a product of:
(a) introducing a hydrazyl group(s) or an amino group(s) by converting at least one carboxyl groups of hyaluronic acid into N-substituted amide or ester group(s) having a substituent containing a hydrazyl or amino group; and
(b) introducing an unsaturated C—C bond-containing group(s) into the resulting hyaluronic acid derivative having a hydrazyl or amino group(s).
4. The sustained-release drug carrier of claim 1, wherein the hyaluronic acid derivative having an unsaturated C—C bond(s) contains at least one repeating structure represented by Formula (IV)

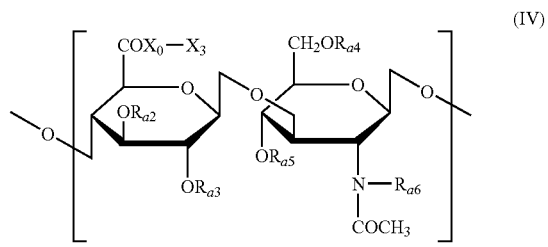

wherein
$X_0$ represents —O— or —N(—$R_1$)—,
$X_3$ represents —$Y_1$-$Q_1$-$Y_2$—N(—$R_2$)—$Y_3$-$Q_4$ or —N(—$R_2$)—$Y_3$-$Q_4$,
$R_1$ represents a hydrogen atom, a linear or branched $C_{1-10}$ alkyl group, a linear or branched $C_{1-10}$ hydroxyalkyl group, a polyalkylene oxide group, a polypeptide group, or a polyester group,
$R_{a2}$, $R_{a3}$, $R_{a4}$, $R_{a5}$ and $R_{a6}$ each independently represent a hydrogen atom, a linear or branched $C_{1-6}$ alkyl group, a linear or branched $C_{1-6}$ alkenyl group, a linear or branched $C_{1-6}$ alkynyl group, a linear or branched $C_{1-6}$ alkylcarbonyl group, a linear or branched $C_{1-6}$ alkenylcarbonyl group, a linear or branched $C_{1-6}$ alkynylcarbonyl group, or —$SO_2OH$,
$Y_1$ represents a single bond, —N(—$R_3$)CO—, —N(—$R_3$)—, —CO—, or —$CH_2$CO—,
$Y_2$ represents a single bond, —CON(—$R_4$)—, or —N(—$R_4$)—
$Y_3$ represents a single bond, —CO—, —N(—$R_5$)CO—, —N(—$R_5$)—, or —$CH_2$CO—,
$Q_1$ represents a linear or branched $C_{1-10}$ alkylene group, a linear or branched $C_{1-10}$ hydroxyalkylene group, a polyalkylene oxide group, a polypeptide group, or a polyester group,
$R_2$, $R_3$, $R_4$ and $R_5$ each independently represent a hydrogen atom, a linear or branched $C_{1-10}$ alkyl group, a linear or branched $C_{1-10}$ hydroxyalkyl group, a polyalkylene oxide group, a polypeptide group, or a polyester group, and
$Q_4$ represents a linear or branched $C_{2-10}$ alkenyl group, or a linear or branched $C_{2-10}$ alkynyl group.
5. The sustained-release drug carrier of claim 1, wherein the hyaluronic acid derivative having an unsaturated C—C bond(s) contains a repeating structure A of Formula (III):

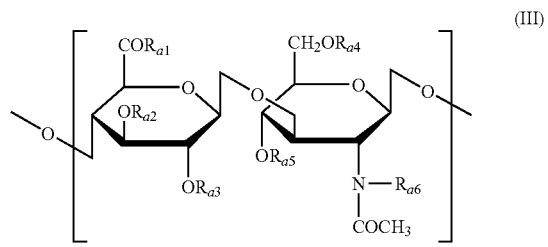

wherein
$R_{a1}$ represents a hydroxyl group, an amino group which may be mono- or di-substituted with a linear or branched $C_{1-6}$ alkyl group, or a linear or branched $C_{1-6}$ alkoxy group, or $R_{a1}$ may form a carboxylate salt with a cation selected from the group consisting of sodium ion, potassium ion, calcium ion, magnesium ion, lithium ion and an optionally substituted ammonium ion, and $R_{a2}, R_{a3}, R_{a4}, R_{a5}$ and $R_{a6}$ each independently represent a hydrogen atom, a linear or branched $C_{1-6}$ alkyl group, a linear or branched $C_{1-6}$ alkenyl group, a linear or branched $C_{1-6}$ alkynyl group, a linear or branched $C_{1-6}$ alkylcarbonyl group, a linear or branched $C_{1-6}$ alkenylcarbonyl group, a linear or branched $C_{1-6}$ alkynylcarbonyl group, or —SO$_2$OH;

and the repeating structure C represented by Formula (IV):

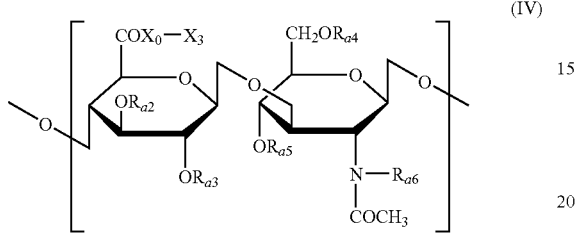

wherein $X_0$ represents —O— or —N(—R$_1$)—, $X_3$ represents —Y$_1$-Q$_1$-Y$_2$—N(—R$_2$)—Y$_3$-Q$_4$ or —N(—R$_2$)—Y$_3$-Q$_4$ $R_1$ represents a hydrogen atom, a linear or branched $C_{1-10}$ alkyl group, a linear or branched $C_{1-10}$ hydroxyalkyl group, a polyalkylene oxide group, a polypeptide group, or a polyester group, $R_{a2}, R_{a3}, R_{a4}, R_{a5}$ and $R_{a6}$ each independently represent a hydrogen atom, a linear or branched $C_{1-6}$ alkyl group, a linear or branched $C_{1-6}$ alkenyl group, a linear or branched $C_{1-6}$ alkynyl group, a linear or branched $C_{1-6}$ alkylcarbonyl group, a linear or branched $C_{1-6}$ alkenylcarbonyl group, a linear or branched $C_{1-6}$ alkynylcarbonyl group, or —SO$_2$OH, $Y_1$ represents a single bond, —N(—R$_3$)CO—, —N(—R$_3$)—, —CO—, or —CH$_2$CO—, $Y_2$ represents a single bond, —CON(—R$_4$)—, or —N(—R$_4$)—, $Y_3$ represents a single bond, —CO—, —N(—R$_5$)CO—, —N(—R$_5$)—, or —CH$_2$CO—, $Q_1$ represents a linear or branched $C_{1-10}$ alkylene group, a linear or branched $C_{1-10}$ hydroxyalkylene group, a polyalkylene oxide group, a polypeptide group, or a polyester group, $R_2, R_3, R_4$ and $R_5$ each independently represent a hydrogen atom, a linear or branched $C_{1-10}$ alkyl group, a linear or branched hydroxyalkyl group, a polyalkylene oxide group, a polypeptide group, or a polyester group, and $Q_4$ represents a linear or branched $C_{2-10}$ alkenyl group, or a linear or branched $C_{2-10}$ alkynyl group, wherein the abundance ratio between the repeated structures A and C is 95:5 to 10:90.

6. The sustained-release drug carrier of claim 1, wherein the mercapto group-containing compound is dithiothreitol.

* * * * *